United States Patent [19]

Shinozaki et al.

[11] 4,267,641
[45] May 19, 1981

[54] RADIOGRAPHIC FILM INCLINOMETER

[75] Inventors: Tamotsu Shinozaki, South Burlington, Vt.; Thomas E. Gallant, Norwood, Mass.; Robert S. D. Deane, Burlington; Daniel Cunningham, Milton, both of Vt.

[73] Assignee: Picker Corporation, Cleveland, Ohio

[21] Appl. No.: 55,776

[22] Filed: Jul. 9, 1979

[51] Int. Cl.³ .............................................. G01C 9/10
[52] U.S. Cl. ...................................................... 33/365
[58] Field of Search ................... 33/365, 366; 250/510

[56] References Cited

U.S. PATENT DOCUMENTS

| | | | |
|---|---|---|---|
| 2,433,480 | 12/1947 | Rendich | 33/365 X |
| 2,494,278 | 1/1950 | Badovinac | 33/365 |
| 2,611,188 | 9/1952 | Bell | 33/365 |

*Primary Examiner*—Charles E. Phillips

*Attorney, Agent, or Firm*—Watts, Hoffmann, Fisher & Heinke Co.

[57] ABSTRACT

An inclinometer (I) for attachment to a radiographic film cassette (C) for indicating on radiographic film in the cassette the angular orientation of the film during exposure. A cylindrical body (10) defines therein an array of cylindrical passages (12) having axes each orthogonal to the body cylinder axis. Each passage axis has a rotational orientation about the body axis which differs by approximately 10 degrees from that of its respective neighbors. A radiopaque spherical indicator element (14) is disposed within each respective column for gravity responsive movement as a function of angular orientation of the body structure. Clamping means (20, 22) holds the body structure superimposed over a portion of radiographic film to be exposed. The relative positions of the indicator elements within their respective passages appears on the exposed film, indicating the angular disposition of the film during exposure.

7 Claims, 4 Drawing Figures

RADIOGRAPHIC FILM INCLINOMETER

DESCRIPTION

1. Technical Field

This invention relates to the field of radiography, and more particularly to apparatus and method for indicating, on a portion of exposed radiographic film, angular orientation to the horizontal of the film at the time the exposure was made.

2. Background Art

In medical diagnostic radiography, a piece of X-ray sensitive radiographic film, often encased in a cassette, is placed against a portion of a patient's body. An x-ray source produces x-rays which penetrate the patient's body and expose the radiographic film in a pattern. The pattern yields information concerning internal structure and/or condition of the patient's body.

The results of some radiographic diagnostic procedures, involving studies of vascular condition, and of the presence of fluid within the body, are gravity dependent. Consequently, information obtained in such studies is affected by the orientation to the horizontal of the patient's body, and therefore of the film, during the making of radiographic exposures.

Gravity dependent differences in test results can complicate the task of interpreting the radiographs, and can lead to spurious test results.

This problem can be obviated to some degree by making all similar studies with the body at as upright an orientation as possible. Such a practice facilitates comparison of test results between patients, as well as between repeated procedures done on the same patient.

While this technique can improved consistency of results, the problem of evaluating and interpreting radiographs made in such studies is complicated by the fact that some patients, due to their conditions, should not be moved to an upright position.

Included among gravity dependent diagnostic radiographic procedures are chest x-rays used to identify early signs of congestive heart failure (indicated by blood and fluid flow and collection in the lungs). Other gravity dependent tests include studying fluid accumulation in the pleural cavity, and the condition of blood vessels themselves.

Often, patients for whom such studies are indicated are critically ill in ways which contraindicate movement of the body to upright angles. Moreover, such patients are sometimes encumbered by tubes or connections to monitoring devices, further limiting their mobility.

The requirement that gravity dependent studies be done on different patients at different body orientations gives rise to an as yet unfulfilled need for indicating with some precision the angle of radiographic film orientation at the time a radiographic study is performed.

While it is possible to mark individual portions of radiographic film with indications of film orientation, such as by writing on the film with a wax pencil, such methods of record keeping lack permanence. Indicia can become blurred.

This type of manual record keeping lacks precision, in that errors can occur in correlation between the written indication and individual films.

It is therefore an object of the present invention to provide an apparatus and method for making a permanent indication, integral on a portion of radiographic film, of the film orientation with respect to the horizontal at the time the radiographic exposure was made, by use of the very radiation which exposed the film.

DISCLOSURE OF INVENTION

The present invention overcomes the disadvantages of the prior art as described above by providing an apparatus and method wherein a permanent indication can be incorporated into a radiograph at the time of radiographic exposure to indicate orientation of the radiographic film plate with respect to the horizontal at the instant of exposure. Such an apparatus thus utilizes the exposing radiation for the dual purpose of (1) providing an indication of the inclination of the film upon exposure, and (2) producing diagnostic information.

More specifically, the present invention is embodied by an inclinometer for use with a radiographic film cassette. The inclinometer includes a body structure defining therein a passageway. A radiopaque inclination indicator element is located within the passageway. The indicator element is configured such that it is free to move within the passageway in response to gravity and the changing orientation of the body portion of the inclinometer.

When an inclinometer embodying this invention is superimposed over a piece of radiographic film to be exposed, the indicator element will move within the passageway to a location which is a function of angular orientation of the inclinometer to the horizontal. Since the indicator element is superimposed over the film, and is radiopaque, the location of the indicator element in its passage will appear on the exposed film.

Thus, once the film is exposed with the inclinometer superimposed thereover, the radiographic film will develop a permanent and inseparable indication of the inclination of the film at the time the exposure was made.

In accordance with a more specific feature of this invention, the inclinometer apparatus includes a body structure defining an array of columns extending therewithin. Each column is orthogonal to a predetermined axis and has a unique rotational angular disposition with respect to that axis. A radiopaque indicator element is located within each column, as described above.

Thus, the angular inclination of the radiographic film is indicated by the relative positions of the various indicator elements in their respective differently oriented columns.

In accordance with another specific feature of the invention, the body structure of the inclinometer is connected to a base means for removably superimposing the inclinometer body portion over a portion of radiographic film in a cassette.

A still more specific feature of the invention is the inclusion on the base means of radiopaque indicia superimposable over the film. Such indicia can include the representation of the letters "R" or "L", for indicating whether the radiographic film image is of a right or left member of a patient's body.

In accordance with another specific feature, the body portion is substantially cylindrical, with the columns having axes each perpendicular to and intersecting the cylinder axis. Each column is substantially linear, and is rotationally disposed with respect to the cylinder axis at a unique angular position ten degrees different from that of its immediate neighbors. Thus, the axes of the columns intersect the surface of the cylindrical body in a substantially helical pattern.

The present invention will be understood in more detail by reference to the following best mode description and to the drawings, in which:

BEST MODE FOR CARRYING OUT THE INVENTION

Figure 1:
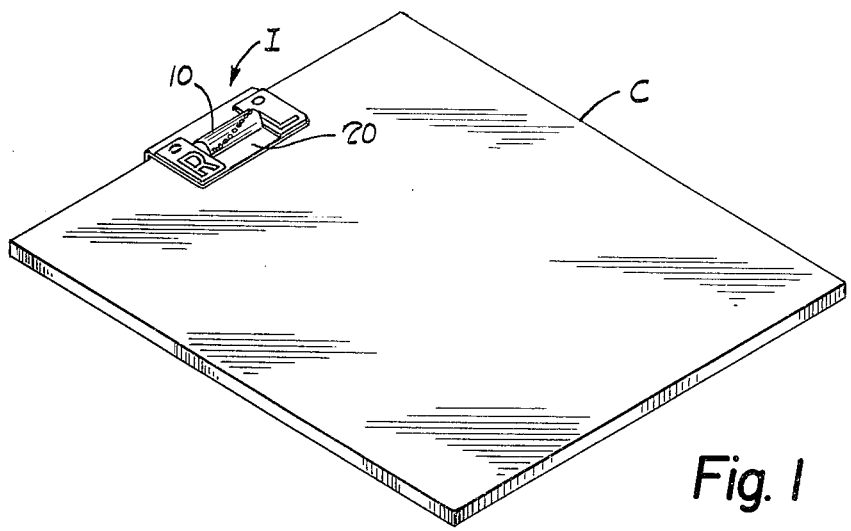
FIG. 1 is a perspective drawing illustrating an embodiment of the present invention, in partially hidden form.

FIG. 1 generally shows an inclinometer I which is removably attachable to a cassette C for holding radiographic film. The Inclinometer has a body portion 10. When the body portion 10 is superimposed stationary relative to a portion of radiographic film to be exposed, the inclinometer indicates radiographic film orientation to the horizontal as the time radiographic exposure is made.

Figure 2:
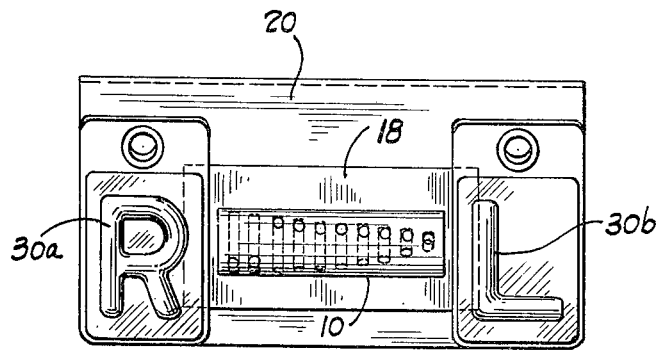
FIG. 2 is a top view of the embodiment shown in FIG. 1.
Figure 3:
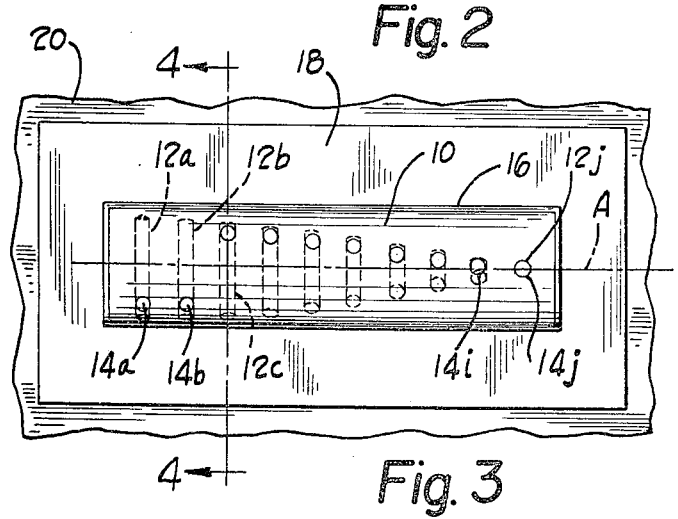
FIG. 3 is a top view of the embodiment of FIG. 2, partially broken away.
Figure 4:
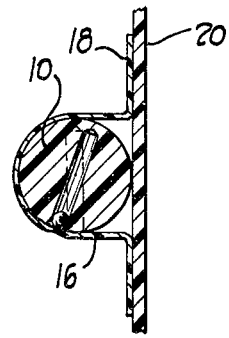
FIG. 4 is an end cross sectional view of the embodiment as illustrated in FIG. 3.

Referring to FIGS. 2 and 3, the inclinometer is shown in more detail. The body portion 10 is preferably made from a cylindrical portion of plastic commonly known by the designation "Lucite". The generally cylindrical body portion is approximately 9 millimeters in diameter and about 5 centimeters in length.

An array of generally cylindrical columns 12a–12j are drilled through the body portion 10. The axes of each column 12a–12j are orthogonal to and intersect the axis A of the body cylinder. Each column is approximately 2 millimeters in diameter.

The axis of each column has a unique rotational orientation with respect to the body cylinder axis A. More specifically, the rotational orientation of each column axis differs from that of each of its neighbors by 10 degrees. The axis of each column, proceeding left to right in FIG. 3, is oriented by 10 degrees more in a counterclockwise direction (as viewed from the left end of FIG. 3) from the immediately proceeding column. Thus, the points of intersection of the column axes with the surface of the cylindrical body member 10 form a generally helical pattern.

A single lead ball indicator element, approximately 1.5 millimeters in diameter, is located in each column. The lead balls are indicated as 14a–14j. A plastic member 16 covers the exterior of the body cylinder 10, in order to retain each of the spherical lead indicator elements in its respective column.

Since the diameters of the indicators elements 14a–14j are slightly less than the diameters of the columns 12a–12j, the indicator elements are free to move within their respective columns in response to gravity, i.e., in response to differing orientation of the body portion 10 about its axis A.

Thus, the angular orientation of the body portion 10 about its axis can be determined within limits by noting the respective positions of the spherical lead indicator elements in their respective columns. For approximately each 10 degrees of clockwise rotation, as viewed from the left end of FIG. 3, about the body axis A, an additional ball will fall from one end of its column to the other. Thus, the orientation of the body portion 10 can be determined within 10 degrees by counting the number of balls that have fallen from one end of their respective columns to the other. In the example illustrated in FIG. 3, the left two indicator elements 14a, 14b have fallen from the generally rearward to the generally forward ends of their respective columns. This condition indicates that the body portion has been rotated approximately 20 degrees from a reference orientation, in which all the indicator elements were located formerly at the generally rearward ends of their respective columns.

A base member 20 is provided for removably superimposing the body portion 10 over a portion of radiographic film to be exposed.

The body portion 10 is suitably fixed to the base member 20.

By superimposing the body portion 10, with its movable indicator elements 14, over a portion of the radiographic film to be exposed, the relative positions of the indicator elements 14 in their respective columns will appear on the radiographic film. This pattern of indicator element location indicates to a viewer of the radiograph the approximate orientation of the radiographic film, to the horizontal about the axis A of the body portion 10.

Preferably, radiopaque indicia 30a, 30b are attached to the base 20. As shown in FIG. 2, the indicia preferably chosen include the letters "R" and "L". These indicia are suitably made from a radiopaque material, such as lead.

By suitable placement of the inclinometer relative to the cassette, a user can position either the radiopaque "R" or the radiopaque "L" over the portion of radiographic film to be exposed. This indicia can be used to indicate whether the radiograph represents an image of a right or left portion of a patient's body.

It is to be understood that the specific disclosure made here is illustrative, rather than exhaustive, of the invention. It should be recognized that one of ordinary skill could make certain additions, deletions and changes to the specific structure disclosed here without departing from the spirit of the present invention, or from its scope, as defined by the appended claims.

We claim:

1. An inclinometer for use with radiographic film, the inclinometer comprising:
  (a) body structure defining an array of columns lying in parallel planes and extending within said body structure said columns being substantially orthogonal to an axis and having different respective radial dispositions with respect to the axis, and
  (b) substantially radiopaque inclination indicating material disposed for gravity responsive movement within the respective columns as a function of orientation of the body structure relative to the horizontal.

2. The inclinometer of claim 1, further comprising:
 a base member for facilitating removably positioning the inclinometer fixed relative to a radiographic film cassette.

3. The inclinometer of claim 2, further comprising: radiopaque indicia disposed on said base member.

4. The inclinometer of claim 3, wherein said indicia comprise:
 a representation of the letter "R", and a representation of the letter "L".

5. The inclinometer of claim 1, further comprising:
  (a) a base member attached to said body structure, and (b) radiopaque indicia disposed on said base member.

6. Apparatus for use in association with a radiographic film cassette for indicating the angular disposition of the cassette during radiographic exposure, said apparatus comprising:
 (a) generally cylindrical body structure defining an array of substantially cylindrical columns therein, said columns each having axes substantially orthogonal to and intersecting the body cylinder axis and having rotational orientation with respect to the axis respectively differing by the same predetermined angular amount from the rotational orientation of adjacent columns, such that axes of the array of columns collectively define a helical pattern at the body cylinder surface;
 (b) a substantially spherical radiopaque indicator element disposed in each column for gravity responsive movement therewithin;
 (c) structure for retaining each of said radiopaque indicator elements within its respective column;
 (d) base structure attached to said body structure for removably attaching the body structure to a radiographic film cassette such that the body structure is superimposed over a portion of radiographic film to be exposed, and
 (e) radiopaque indicia disposed on a portion of the base structure for superimposition over a portion of the radiographic film to be exposed.

7. The apparatus of claim 6, wherein:
 the axis of each of said columns has a rotational angular disposition with respect to the body axis differing by approximately 10 degrees from that of adjacent columns.

* * * * *